United States Patent
Bertolini et al.

(10) Patent No.: US 7,534,885 B2
(45) Date of Patent: May 19, 2009

(54) PROCESS AND INTERMEDIATES FOR PREPARING EMTRICITABINE

(75) Inventors: Giorgio Bertolini, Sesto San Giovanni (IT); Maurizio Deleo, Milan (IT); Marco Frigerio, Milan (IT); Massimo Losa, Pogliano Milanese (IT); Maurizio Velati, Mezzana Rabattone (IT)

(73) Assignee: Archimica S.r.l., Milan (IT)

( * ) Notice: Subject to any disclaimer, the term of this patent is extended or adjusted under 35 U.S.C. 154(b) by 285 days.

(21) Appl. No.: 10/550,718

(22) PCT Filed: Mar. 19, 2004

(86) PCT No.: PCT/IB2004/000924

§ 371 (c)(1),
(2), (4) Date: Sep. 23, 2005

(87) PCT Pub. No.: WO2004/085432

PCT Pub. Date: Oct. 7, 2004

(65) Prior Publication Data

US 2006/0189805 A1  Aug. 24, 2006

(30) Foreign Application Priority Data

Mar. 24, 2003  (IT) .......................... MI2003A0578

(51) Int. Cl.
C07D 411/04 (2006.01)
A61K 31/513 (2006.01)
A61K 31/12 (2006.01)

(52) U.S. Cl. ..................................... 544/317; 544/318

(58) Field of Classification Search ................. 544/317, 544/318
See application file for complete search history.

(56) References Cited

U.S. PATENT DOCUMENTS

| 5,204,466 A | 4/1993 | Liotta |
| 5,538,975 A | 7/1996 | Dionne |
| 5,696,254 A | 12/1997 | Mansour |
| 5,852,027 A | 12/1998 | Liotta |
| 5,892,025 A | 4/1999 | Liotta |
| 6,051,709 A | 4/2000 | Goodyear |
| 6,329,522 B1 | 12/2001 | Hill |

FOREIGN PATENT DOCUMENTS

EP  0515157  11/1992

OTHER PUBLICATIONS

Chu, CK; et al., "Synthesis and Antiviral Activity of Oxaselenolane Nucleosides", J. Med. Chem., 2000, pp. 3906-3912, vol. 43.
Jeong, LS; et al., "Asymmetric Synthesis and Biological Evaluation of Beta-L-(2R,5S)- and Alpha-L-(2,R,5R-1,3-Oxathiolane-Pyrimidine . . . ", J. Med Chem., 1993, pp. 181-195, V36, N2.

*Primary Examiner*—Venkataraman Balasubramanian
(74) *Attorney, Agent, or Firm*—ProPat, L.L.C.

(57) ABSTRACT

A process is disclosed for the stereo-selective preparation of emtricitabine, which allows the desired product to be obtained in good yield and without the use of chromatographic techniques. The process for the production of emtricitabine of the formula (Ia)

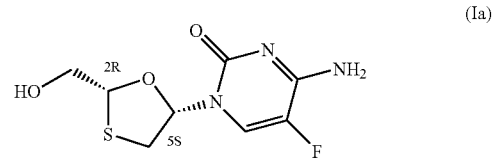

(Ia)

is characterized by the formation and isolation of intermediate compounds of formula (XIa)

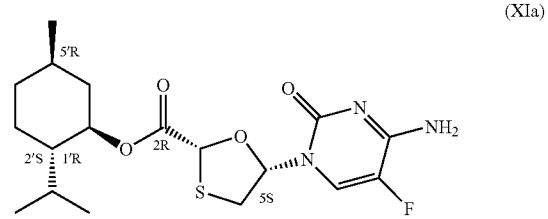

(XIa)

in salified form. Emtricitabine is a known antiviral drug.

9 Claims, No Drawings

PROCESS AND INTERMEDIATES FOR PREPARING EMTRICITABINE

The present invention relates to a novel process for preparing emtricitabine, and more particularly a process for preparing emtricitabine characterized by the formation and isolation of intermediate compounds in salified form.

Emtricitabine is a known antiviral drug of formula

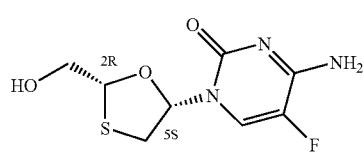
(Ia)

also known under the trade name Coviracil® or FTC (Merck Index, Ed. 2001, No. 3597).

The compound, as illustrated in FIG. Ia, is the cis enantiomer having the 2R, 5S absolute configuration, and its chemical name is 4-amino-5-fluoro-1-[(2R, 5S)-2-(hydroxymethyl)-1,3-oxathiolan-5-yl]-2(1H)-pyrimidin-2-one (CAS). The other optical isomers, i.e. the cis 2S, 5R enantiomer (Ib) and the trans enantiomers 2S, 5S (Ic) and 2R, 5R (Id), have lower therapeutic activity and are therefore found to be of reduced interest in application.

EP 0 526 253 A1 discloses Emtricitabine, salts thereof and the use in the treatment of viral infections.

Various routes for synthesizing emtricitabine are described in the literature.

For example, in international patent application WO 92/14743 (Emory University), the racemic mixture of cis isomers is prepared via standard reactions and by resolution, mainly enzymatic resolution, gives the desired 2R, 5S enantiomer.

Stereoselective synthetic routes were subsequently developed, which, by means of the use of chiral auxiliaries such as menthol, allow the desired stereochemistry to be induced and allow emtricitabine to be obtained directly as a single enantiomer. US patent U.S. Pat. No. 5,696,254 (BioChem Pharma Inc.) illustrates just this type of synthetic approach, applied to the synthesis of emtricitabine, as shown, for example, in Scheme 2B (columns 13 and 14) below:

SCHEME 2B

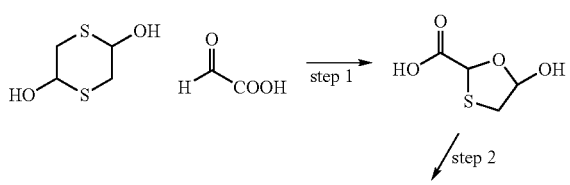

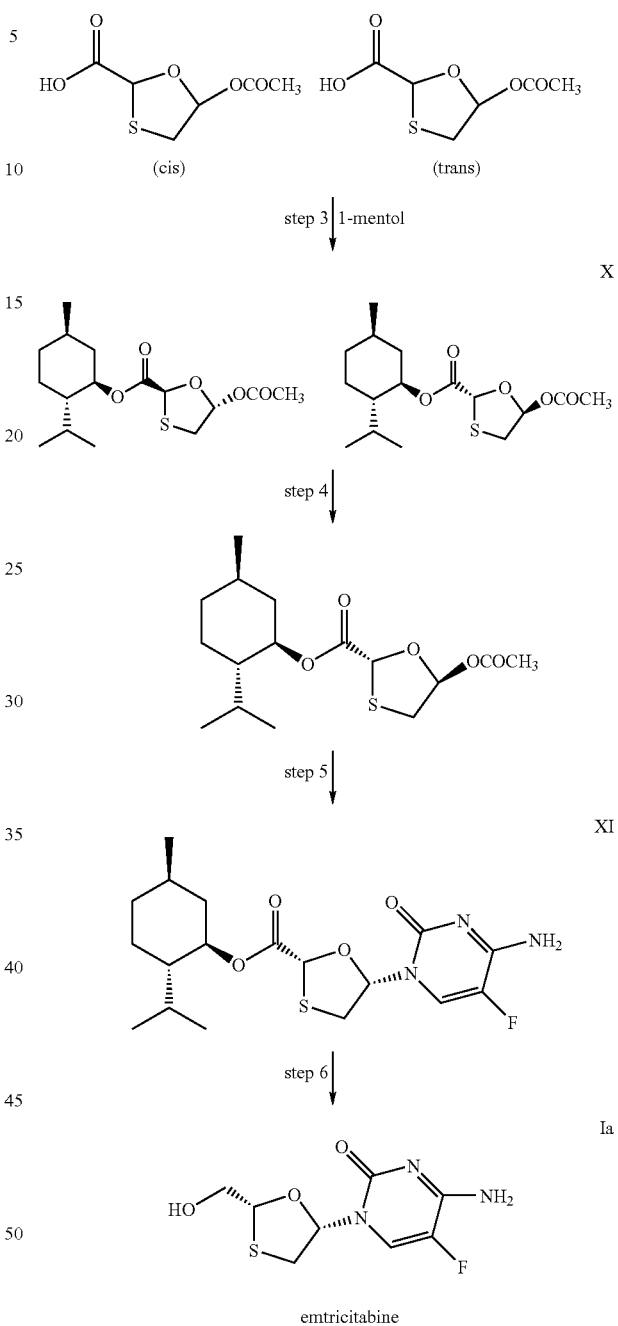

In this scheme, the trans oxathiolane is prepared (step 1, VIII) which, when acetylated (step 2, IX) and condensed with 1-menthol, leads to the mixture of intermediate diastereoisomers (step 3, X). The desired diastereoisomer is isolated by fractional crystallization (step 4) and coupled with silylated 5-fluorocytosine (III) (step 5), leading to the derivative XI (which is referred to hereinbelow as XIa), which, finally, by reductive removal of the chiral auxiliary (step 6), gives emtricitabine (right-hand columns 15-16, erroneously represented with inversion of configuration in position 5 of the oxathiolane).

The chiral auxiliary used is 1-menthol (II), the chiral centres of which have the 1'R, 2'S, 5'R absolute configuration, as illustrated below:

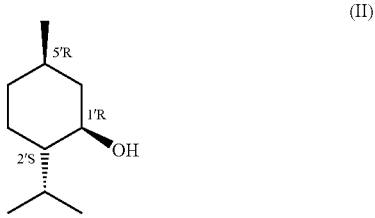

However, in the experimental section of the patent, discrepancies are observed relating to the stereochemistry of the intermediates used to obtain emtricitabine.

In fact, Example 21 (column 43) correctly asserts that to prepare emtricitabine, the formula of which is clearly given at the start of that example, the final reduction should be performed on the compound (1'R, 2'S, 5'R)-menthyl 5S-(5"-fluorocytosin-1-yl)-1,3-oxathiolane-2R-carboxylate—i.e. on intermediate XIa of scheme 2B above—as illustrated below:

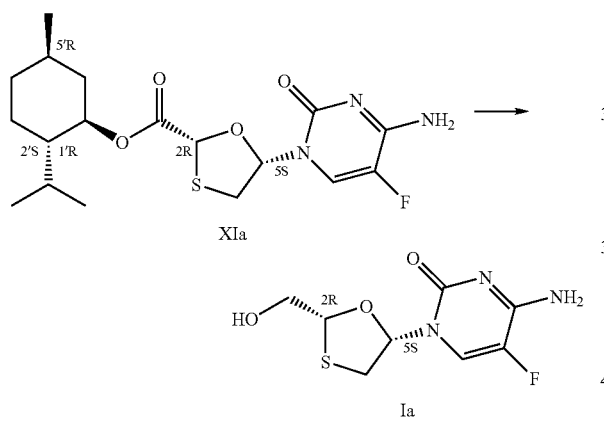

The correct stereochemistry of this sequence, i.e. the use of L-menthol to induce the desired chirality corresponding to emtricitabine, was confirmed experimentally by us and subsequently reinforced as described in U.S. Pat. No. 6,051,709 (Glaxo), which will be discussed later.

In the experimental section of U.S. Pat. No. 5,696,254 (BioChem Pharma Inc.) the preparation of the desired intermediate XIa (having the 1'R, 2'S, 5'R chirality on the menthol and the 2R, 5S chirality on the oxathiolane) does not, however, appear, since Example 18 relates to the derivative XI inverted on the oxathiolane (XIb, 1'R, 2'S, 5'R-2S, 5R), which is thus unsuitable for producing emtricitabine, whereas Example 19 relates to the derivative XI inverted on the menthol (XIc, 1'S, 2'R, 5'S-R2,5S).

Also, U.S. Pat. No. 6,051,709 (Glaxo), mentioned above, describes a stereoselective process for the synthesis of cis nucleosides, this process differing from the above process essentially by the use of leaving groups (L) other than acetate—such as halo, cyano or sulphonate—in the coupling reaction of the intermediate X with the activated 5-fluorocytosine III.

However, the experimental illustration is limited to the preparation of the non-fluoro analogue of emtricitabine, known as lamivudine (Merck Index, Ed. 2001, No. 5367), as illustrated in scheme 1, columns 9-10, without any indication regarding the actual process yields. Example 1 describes the preparation of 5-hydroxyoxathiolane required by reacting 1-menthyl glyoxalate and dithianediol (part a, column 10), and the subsequent formation of the chloro derivative (part b, column 10) and its coupling reaction with cytosine silylate (last paragraph, column 10—first paragraph, column 11). The resulting product, which precipitates from the reaction medium, is recovered by simple filtration and subjected to reductive removal of the chiral auxiliary to give the crude lamivudine, which is purified, not by direct crystallization of the base but of the salified form, in particular of the salicylate. It is obvious that, by this procedure, a subsequent basic treatment will be necessary to release the lamivudine base from its salt.

This procedure, which does not appear to present any particular implementation difficulties in the case of lamivudine, becomes entirely inapplicable when used for the preparation of emtricitabine.

Specifically, we have been able to verify experimentally that the product XIa, resulting from the coupling reaction of the activated 5-fluorocytosine III with the appropriate acetate X (scheme 2B of U.S. Pat. No. 5,696,254) or with the corresponding analogue of formula

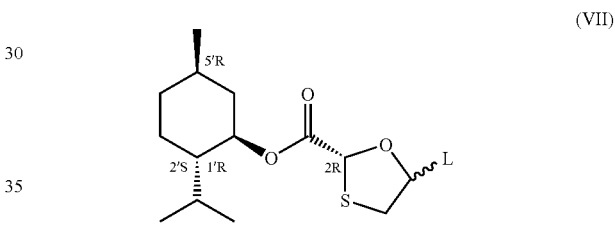

containing another leaving group (L) instead of acetate (U.S. Pat. No. 6,051,709), is not a filterable solid at all as in the case of lamivudine, but a gel that is inseparable from its mother liquors by simple filtration, and can be purified only by chromatography.

The entire stereoselective synthesis discussed hereinabove, when applied to emtricitabine, thus becomes difficult to implement industrially on account of the problems of isolation and purification of the key intermediate XIa.

We have now found a novel process that may be applied industrially for the stereo-selective preparation of emtricitabine, which allows the desired product to be obtained in good yield and without the use of chromatographic techniques, which are particularly disadvantageous from a practical point of view.

One subject of the present invention is thus a process for preparing emtricitabine of formula

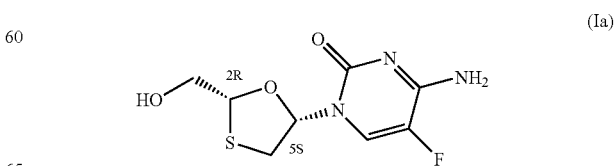

which comprises the salification reaction of the intermediate compound of formula

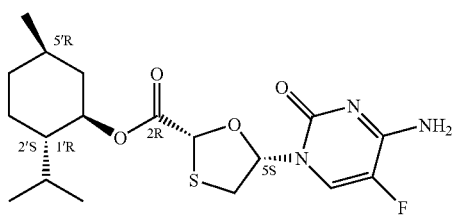

(XIa)

dissolved in a suitable solvent, by treatment with organic or mineral acids to give the corresponding salt, which is insoluble or partially insoluble in the said solvent, in readily isolable solid form. These salts are not known in the literature.

The intermediate compound of formula XIa may be prepared by applying one of the methods discussed previously, for example by condensing the intermediate X (acetate) with the activated 5-fluorocytosine III, by analogy with the description given in U.S. Pat. No. 5,696,254 (Examples 18 and 19, in which the intermediates XIb and XIc are prepared respectively) and as illustrated below:

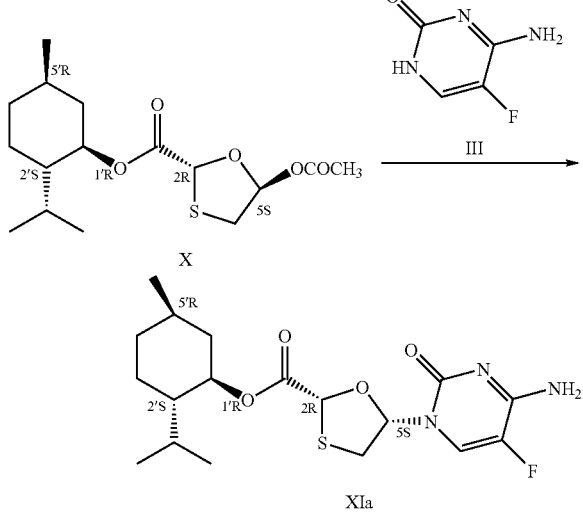

or as shown in U.S. Pat. No. 6,051,709, via the same coupling reaction, in which other leaving groups L (VII) are used instead of acetate:

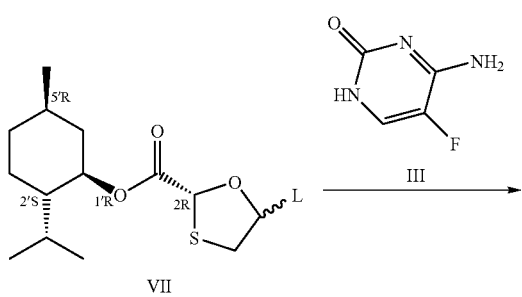

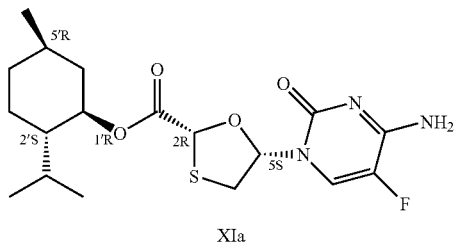

In this case, the stereochemistry of the carbon in position 5 of the oxathiolane ring of compound VII may vary depending on the type of leaving group and on the mechanism of the nucleophilic substitution reaction, as is well known to those skilled in the art, and will be appropriately selected to obtain the correct chirality of compound XIa (5S).

The condensation reaction now illustrated may thus be generally represented by the following scheme:

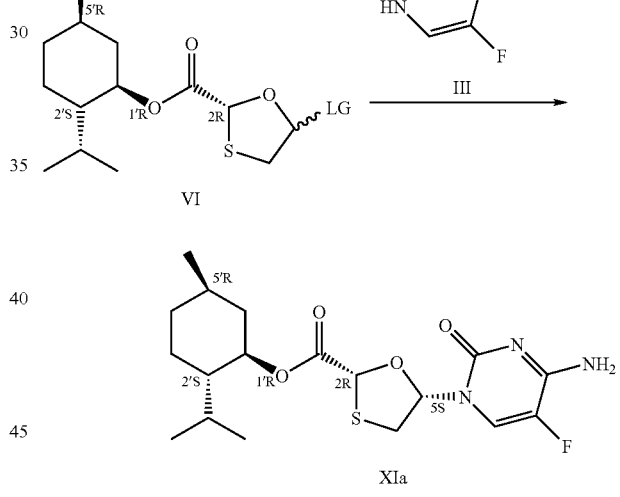

in which the group LG represents any leaving group, provided that it is suitable for giving the condensation reaction under consideration.

Preferably, LG is chosen from acetate, halo, cyano, optionally halogenated alkylsulphonates, or arylsulphonates, such as, for example, chloro, bromo, iodo, methanesulphonate, triflate, tosylate and benzenesulphonate, and even more preferably from chloro and acetate.

Compound of formula VI may generally be prepared as described in the abovementioned prior art or according to standard reactions for conversion of the OH group of the 2'S-isopropyl-5'R-methyl-1'R-cyclohexyl ester of (2R, 5R)-5-hydroxy[1,3]oxathiolane-2-carboxylic acid V (described in U.S. Pat. No. 6,051,709, Example 1a), into the appropriate leaving group LG according to the scheme:

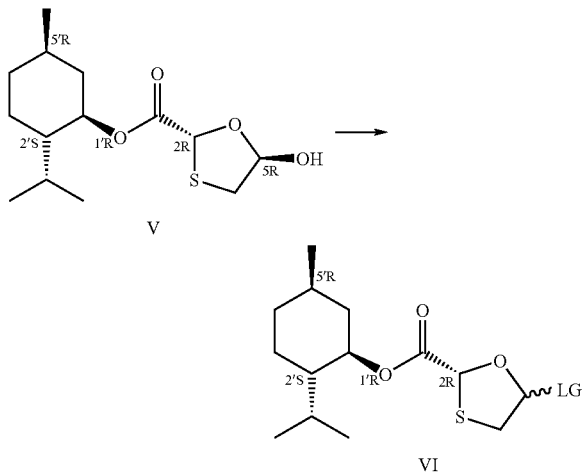

In the condensation reaction illustrated above, the 5-fluorocytosine III may be activated under the conditions described in U.S. Pat. No. 5,696,254 and U.S. Pat. No. 6,051,709 or using other silylating conditions, for example by treatment with trialkylsilyl halides such as trimethylsilyl chloride, or with mixtures of silylating agents in the presence of catalysts, such as ammonium sulphate, and condensed with the appropriate intermediate VI to give the desired compound XIa.

Another subject of the present invention is thus a process for preparing emtricitabine, characterized by the formation of the salt described above, which further comprises the condensation reaction between 5-fluorocytosine of formula

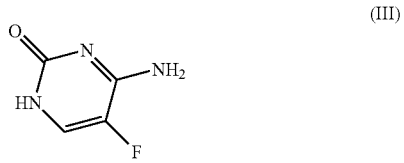

in suitably activated form, and the compound of formula

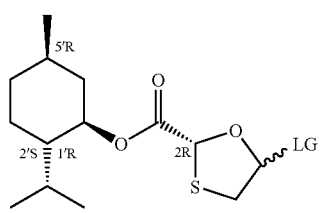

in which LG represents a leaving group chosen from acetate, halo, cyano, optionally halogenated alkylsulphonates, or arylsulphonates, to give the compound of formula XIa.

We have verified experimentally that, independently of the route of preparation, compound XIa does not separate out from the reaction medium, either by addition of hexane, as takes place, however, in the case of the non-fluoro analogue (Example 1, column 11, lines 9-11), or by centrifugation, as for the diastereoisomers XIb and XIc (Examples 1 and 19, U.S. Pat. No. 5,696,254), but rather is in the form of an unfilterable gel.

According to the present invention, the said crude intermediate XIa, obtained after working up the reaction mixture under standard conditions, is dissolved in a suitable solvent and subjected to salification, to give an insoluble or partially insoluble salt of compound XIa in readily isolable solid form.

The expression "readily isolable solid form" means an amorphous or crystalline, preferably crystalline, solid which separates out cleanly from the reaction mixture without including significant amounts of solvent or impurities, and which is then easily isolable by filtration or via similar common techniques.

The solvent used in the salification reaction must be capable of readily dissolving the intermediate XIa and not its salt, this salt generally precipitating spontaneously from the medium.

Suitable solvents are generally alcohols, such as methanol, ethanol and isopropanol, hydrocarbons such as toluene, esters such as ethyl acetate, propyl acetate, isopropyl acetate, butyl acetate and isobutyl acetate, and ethers such as tetrahydrofuran and dioxane, chlorinated solvents such as methylene chloride, or mixtures of these solvents, preferably alcohols, esters or ethers or mixtures thereof, even more preferably methanol, isopropanol and ethyl acetate.

Acids that may be used are generally organic acids, for instance mono- or polycarboxylic acids or sulphonic acids, and mineral acids provided that they are capable of salifying the amino group of compound XIa, for instance fumaric acid, maleic acid, lactic acid, salicylic acid, succinic acid, glycolic acid, tartaric acid, acetic acid, citric acid, formic acid, benzoic acid, malonic acid, oxalic acid, hydrochloric acid, hydrobromic acid, sulphuric acid, nitric acid, perchloric acid, phosphoric acid, p-toluenesulphonic acid, methanesulphonic acid, 2-naphthalenesulphonic acid, benzenesulphonic acid and 4-chlorobenzenesulphonic acid, preferably oxalic acid, succinic acid, maleic acid, methanesulphonic acid, 4-chlorobenzenesulphonic acid and hydrochloric acid, and even more preferably oxalic acid.

The amount of acid used is at least equal to the stoichiometric amount.

The precipitation of the salt of compound XIa may optionally be promoted via conventional techniques such as cooling of the solution, initiation by addition of crystals of the same salt, or other methods that are well known to those skilled in the art.

The precipitated salt of the compound of formula XIa is generally recovered by filtration, centrifugation or decantation, preferably by filtration, although other conventional methods known to those skilled in the art may also be used.

The filtration is formed using standard filtration means such as press filters, static filters, centrifuges and other standard industrial filtration techniques.

The salt of compound XIa with the said organic or mineral acids constitutes a further subject of the present invention. The said salt may be obtained by salification of compound XIa with fumaric acid, maleic acid, lactic acid, salicylic acid, succinic acid, glycolic acid, tartaric acid, acetic acid, citric acid, formic acid, benzoic acid, malonic acid, oxalic acid, hydrochloric acid, hydrobromic acid, sulphuric acid, nitric acid, perchloric acid, phosphoric acid, p-toluenesulphonic acid, methanesulphonic acid, 2-naphthalenesulphonic acid, benzenesulphonic acid or 4-chlorobenzenesulphonic acid, preferably with oxalic acid, succinic acid, maleic acid, methanesulphonic acid, 4-chlorobenzenesulphonic acid or hydrochloric acid, and even more preferably with oxalic acid.

The salt of compound XIa isolated as described above may be further purified, for example by crystallization, or subjected to a standard basic treatment to give compound XIa as free base, or, preferably, used directly in the subsequent reaction.

The compound XIa thus obtained generally has a very high purity, which is reflected in a further advantage of the present invention over the processes of the prior art.

Specifically, by using the intermediate XIa of the present process in the subsequent reductive passage, it is possible to obtain emtricitabine Ia in a purity that allows its direct crystallization, as free base, thus making it unnecessary to perform steps of salification/crystallization/liberation of the base—as described for lamivudine in U.S. Pat. No. 6,051,709—or even making it unnecessary to purify the emtricitabine base by chromatography, as takes place in U.S. Pat. No. 5,696,254 (Example 21).

This last aspect of the process of the invention is particularly advantageous when it is considered that final release of the emtricitabine salt suggested by the art can cause the formation of organic or mineral salts that are difficult to remove, for instance triethylamine hydrochloride, which may then contaminate the active principle. In this event, since the process concerns a medicinal product, it will then be necessary to perform further purification steps to ensure the required high standard of purity, with all the entailing operating and economic drawbacks.

However, in the present process, emtricitabine Ia, obtained by the following reductive reaction:

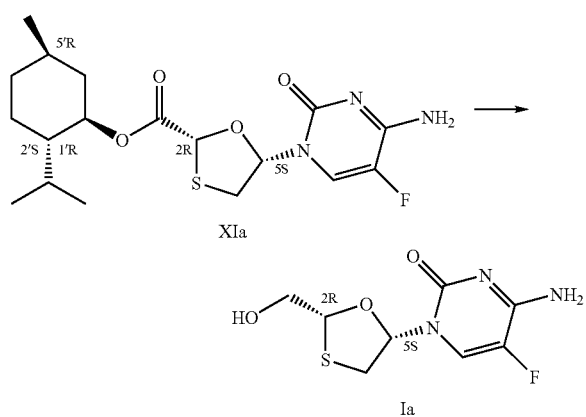

is isolated as a crude product, under the standard conditions for working up reductive reactions of this type, and is subsequently crystallized from suitable solvents such as methylene chloride, alcohols such as isopropanol or esters such as ethyl acetate or isopropyl acetate, or mixtures thereof, for instance methanol and isopropyl acetate, preferably from a mixture of methanol and isopropyl acetate, thus directly forming emtricitabine in high purity and with good yields.

This final reduction reaction may be performed, for example, as described in U.S. Pat. No. 5,696,254 (Example 21) or in U.S. Pat. No. 6,051,709 (Example 1c) or under analogous conditions known to those skilled in the art.

In the present invention, the said reduction is preferably performed by releasing in situ the base of compound XIa from its isolated salt (one-pot reaction) via a standard basic treatment.

It is obvious to those skilled in the art that the process that is the subject of the present invention, in all its variants, will also be applicable to the preparation of the other cis isomer of emtricitabine, i.e. the (2S, 5R) compound Ib. In this case, the salification reaction will be performed on the key intermediate of formula XId, which in turn may be obtained via the same reactions discussed above for the preparation of emtricitabine, except that the chiral auxiliary will be represented by D-menthol.

In one preferred embodiment of the present process, compound V (2'S-isopropyl-5'R-methyl-1'R-cyclohexyl (2R, 5R)-5-hydroxy[1,3]-oxathiolane-2-carboxylate) is converted into the corresponding chloro derivative (VI, LG=Cl) and then reacted with silylated 5-fluorocytosine (III) until the condensation reaction is complete.

Alternatively, compound X (2S-isopropyl-5R-methyl-1R-cyclohexyl (2R, 5S)-5-acetoxy-[1,3]oxathiolane-2-carboxylate) is reacted with silylated 5-fluorocytosine (III) in the presence of Lewis acids until the condensation reaction is complete.

The crude product (XIa) obtained after working up the reaction is dissolved in methanol and salified with oxalic acid. The oxalate compound XIa is separated out by filtration and used in the same form in the subsequent reduction reaction with sodium borohydride. After working up the reaction, a crude product is obtained, which, by crystallization from methanol/isopropyl acetate, gives emtricitabine (Ia) directly.

A number of practical examples will now be given to illustrate the present invention more clearly.

EXPERIMENTAL SECTION

EXAMPLE 1

2'S-Isopropyl-5'R-methyl-1'R-cyclohexyl (2R, 5S)-5-(4-amino-5-fluoro-2-oxo-2H-pyrimidin-1-yl)[1,3]oxathiolane-2-carboxylate oxalate A. Thionyl chloride (24.5 g) was added slowly at about 8° C. to a solution of 2'S-isopropyl-5'R-methyl-1'R-cyclohexyl ester (2R, 5R)-5-hydroxy[1,3]oxathiolane-2-carboxylate (V) (50 g) and methanesulphonic acid (0.2 ml) in methylene chloride (500 ml) and dimethylformamide (15 ml).

The reaction mixture was stirred at 15° C. for about 4 hours and a portion of the methylene chloride (about 350 ml) was then distilled off under vacuum. More methylene chloride (150 ml) was added and some of this (about 50 ml) was evaporated off under vacuum.

B. In another flask, a mixture of 5-fluorocytosine (20 g), hexamethyldisilazane (43 ml) and methanesulphonic acid (0.2 ml) in toluene (75 ml) was refluxed for about 3 hours. The reaction mixture was then distilled under vacuum down to a residue, methylene chloride (about 100 ml) was then added and the mixture was re-evaporated under vacuum. The residue was then redissolved in methylene chloride (250 ml) and triethylamine (28 ml) was added dropwise at 20-25° C. This 5-fluorocytosine silylate mixture was heated to reflux and the solution prepared in point A was slowly added dropwise over 2-3 hours while maintaining the reflux. The reaction mixture thus obtained was refluxed for about 18 hours and then cooled to 20-25° C. and water (150 ml) was added.

The aqueous phase was separated out and the organic phase was washed 5 times with acidified water (5×150 ml) and then with water (150 ml). The solvent was evaporated off under vacuum, the residue was dissolved in methanol (220 ml) and oxalic acid dihydrate (20 g) was added to the solution. The suspension thus obtained was stirred at 20-25° C. for 3 hours and the solid was then filtered off, washed with methanol (30 ml) and dried to give 31.5 g of 2'S-isopropyl-5'R-methyl-1'R-cyclohexyl (2R, 5S)-5-(4-amino-5-fluoro-2-oxo-2pyrimidin-1-yl)[1,3]oxathiolane-2-carboxylate oxalate (m.p. 152-153° C.).

The following salts were also prepared in a similar manner:

2'S-isopropyl-5'R-methyl-1'R-cyclohexyl (2R, 5S)-5-(4-amino-5-fluoro-2-oxo-2H-pyrimidin-1-yl)[1,3]oxathiolane-2-carboxylate maleate (m.p. 155-156° C.).

2'S-isopropyl-5'R-methyl-1'R-cyclohexyl (2R, 5S)-5-(4-amino-5-fluoro-2-oxo-2H-pyrimidin-1-yl)[1,3]oxathiolane-2-carboxylate succinate (m.p. 196-197° C.).

2'S-isopropyl-5'R-methyl-1'R-cyclohexyl (2R, 5S)-5-(4-amino-5-fluoro-2-oxo-2H-pyrimidin-1-yl)[1,3]oxathiolane-2-carboxylate methanesulphonate (m.p. 183-184° C.).

2'S-isopropyl-5'R-methyl-1'R-cyclohexyl (2R, 5S)-5-(4-amino-5-fluoro-2-oxo-2H-pyrimidin-1-yl)[1,3]oxathiolane-2-carboxylate 4-chlorobenzenesulphonate (m.p. 212-213° C.).

2'S-isopropyl-5'R-methyl-1'R-cyclohexyl (2R, 5S)-5-(4-amino-5-fluoro-2-oxo-2H-pyrimidin-1-yl)[1,3]oxathiolane-2-carboxylate hydrochloride (m.p. 208-209° C.).

(2R, 5S)-4-Amino-5-fluoro-1-(2-hydroxymethyl[1,3]oxathiolan-5-yl)-1H-pyrimidin-2-one (emtricitabine)

2'S-Isopropyl-5'R-methyl-1'R-cyclohexyl (2R, 5S)-5-(4-amino-5-fluoro-2-oxo-2H-pyrimidin-1-yl)[1,3]oxathiolane-2-carboxylate (31.5 g) was suspended in a mixture of tetrahydrofuran (140 ml), methanol (28 ml) and water (46.6 g). Potassium bicarbonate (6.5 g) and potassium hydrogen phosphate (14 g) were added. The suspension was cooled to 0-5° C. and a solution of sodium borohydride (11.2 g) and 30% sodium hydroxide (1.1 ml) in water (112 ml) was added slowly over about 2-3 hours. The reaction mixture was then stirred at 20-25° C. for 1 hour. The pH was then brought to 4.0 with 37% hydrochloric acid and the organic solvents were then evaporated off under vacuum. The remaining aqueous phase was extracted three times with toluene (3×70 ml) and the pH of the aqueous solution was then brought to 7.3-7.4 with 30% sodium hydroxide and the water was evaporated off under vacuum. The residue was taken up in isopropanol (100 ml) and evaporated under vacuum, and then taken up again in isopropanol (200 ml). The mineral salts were filtered off and the filtrate was evaporated under vacuum. The crude product was dissolved in methanol (15 ml) and crystallized by adding isopropyl acetate (35 ml). The suspension was stirred overnight at 20° C. and the solid was filtered off and dried to give 5 g of emtricitabine.

EXAMPLE 2

2'S-Isopropyl-5'R-methyl-1'R-cyclohexyl(2R, 5S)-5-(4-amino-5-fluoro-2-oxo-2-H-pyrimidin-1-yl)[1,3]oxathiolane-2-carboxylate oxalate A mixture of 5-fluorocytosine (3.8 g), hexamethyldisilazane (8.1 ml) and methanesulphonic acid (0.02 ml) in toluene (27 ml) was refluxed for about 3 hours. The reaction mixture was then distilled to dryness under vacuum and methylene chloride (about 15 ml) was then added and re-evaporated under vacuum. The residue was then redissolved in methylene chloride (30 ml) and a solution of 2S-isopropyl-5R-methyl-1R-cyclohexyl (2R, 5S)-5-acetoxy[1,3]oxathiolane-2-carboxylate (12.1 g) in methylene chloride (30 ml) was added. Trimethyliodosilane (5.3 ml) was added slowly and the reaction mixture was stirred at room temperature for about 2 hours. The mixture was diluted with methylene chloride (400 ml) and the aqueous phase was washed with saturated sodium metabisulphite solution (100 ml) and then with water (100 ml) and with saturated sodium chloride solution (100 ml).

The organic phase was evaporated off and the residue dissolved in methanol (100 ml) and oxalic acid dihydrate (4.7 g) was added. The suspension thus obtained was stirred at 20-25° C. for 3 hours and the solid was then filtered off, washed with methanol (10 ml) and dried to give 9.2 g of 2'S-isopropyl-5'R-methyl-1'R-cyclohexyl (2R, 5S)-5-(4-amino-5-fluoro-2-oxo-2-H-pyrimidin-1-yl)[1,3]oxathiolane-2-carboxylate oxalate (m.p. 152-153° C.).

The invention claimed is:

1. Process for preparing emtricitabine of formula (Ia)

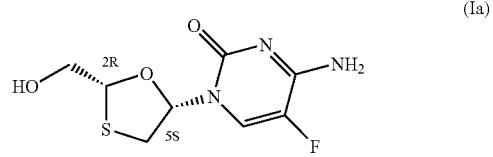

(Ia)

comprising the salification reaction of an intermediate compound of formula (XIa)

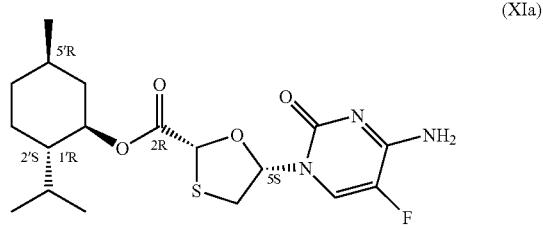

(XIa)

dissolved in a suitable solvent, by treating the intermediate compound of formula (XIa) with an organic or mineral acid to give the corresponding salt, wherein the corresponding salt is in an isolable solid form.

2. The process of claim 1, wherein the solvent is selected from the group consisting of alcohols, hydrocarbons, esters, ethers, chlorinated solvents, and mixtures thereof.

3. The process of claim 2, wherein the solvent is selected from the group consisting of methanol, ethanol, isopropanol, toluene, ethyl acetate, propyl acetate, isopropyl acetate, butyl acetate, isobutyl acetate, tetrahydrofuran, dioxane, methylene chloride, and mixtures thereof.

4. The process of claim 1, wherein said organic or mineral acid is selected from the group consisting of fumaric acid, maleic acid, lactic acid, salicylic acid, succinic acid, glycolic acid, tartaric acid, acetic acid, citric acid, formic acid, benzoic acid, malonic acid, oxalic acid, hydrochloric acid, hydrobromic acid, sulphuric acid, nitric acid, perchloric acid, phosphoric acid, p-toluenesulphonic acid, methanesulphonic acid, 2-naph-thalenesulphonic acid, benzenesulphonic acid, 4-chlorobenzenesulphonic acid, and mixtures thereof.

5. The process of claim 4, wherein said organic or mineral acid is selected from the group consisting of oxalic acid, succinic acid, maleic acid, methanesulphonic acid, 4-chlorobenzene-sulphonic acid, hydrochloric acid, and mixtures thereof.

6. The process of claim 1, further comprising isolating said corresponding salt by filtration.

7. Process for preparing the compound of formula (Ib)

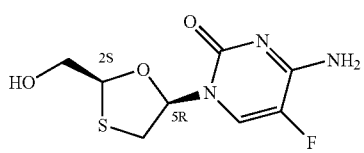
(Ib)

comprising the salification reaction of an intermediate compound of formula (XId)

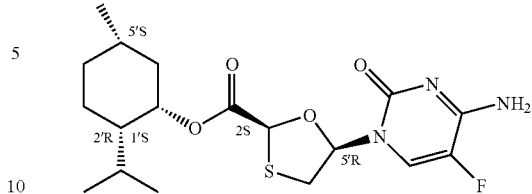
(XId)

dissolved in a suitable solvent, by treating said intermediate compound of formula (XId) with organic or mineral acids to give the corresponding salt, which is insoluble in the said solvent, in readily isolable solid form.

8. The process of claim 2, wherein the solvent is from the group consisting of methanol, isopropanol, ethyl acetate, and mixtures thereof.

9. The process of claim 4, wherein said organic or mineral acid is oxalic acid.

* * * * *